United States Patent [19]

Jordan

[11] 4,325,910
[45] Apr. 20, 1982

[54] AUTOMATED MULTIPLE-PURPOSE CHEMICAL-ANALYSIS APPARATUS

[75] Inventor: Michael Jordan, Merrimack, N.H.

[73] Assignee: Technicraft, Inc., Amherst, N.H.

[21] Appl. No.: 56,688

[22] Filed: Jul. 11, 1979

[51] Int. Cl.³ .................. G01N 21/27; G01N 35/06
[52] U.S. Cl. .................................. 422/64; 250/564; 356/218; 356/434
[58] Field of Search .............. 422/64, 65, 67; 356/180, 184, 188, 246, 434, 218; 364/497, 498; 250/564

[56] References Cited

U.S. PATENT DOCUMENTS

| | | | |
|---|---|---|---|
| 3,728,079 | 4/1973 | Moran | 422/65 |
| 4,054,415 | 10/1977 | Seligson et al. | 422/64 |
| 4,058,367 | 11/1977 | Gilford | 422/67 |
| 4,090,791 | 5/1978 | Siddiqi et al. | 356/184 |
| 4,234,538 | 11/1980 | Ginsberg et al. | 422/64 |

FOREIGN PATENT DOCUMENTS 1501883  2/1978  United Kingdom.

OTHER PUBLICATIONS

Snook et al., "Design Principles of a Computer Controlled Multiplexed Absorptiometer for Reaction Rate Analysis", Jour. of Automatic Chem., Jan. 1979, pp. 72–77.

Primary Examiner—Ronald Serwin
Attorney, Agent, or Firm—Kenway & Jenney

[57] ABSTRACT

Analysis apparatus with flexible multi-analysis capability, suitable for example for biochemical constituent analysis, has a single channel of reaction vessels arranged to receive reagents from any of a battery of reagent reservoirs and has photometer elements from measuring the reaction in each reaction vessel on a repetitive sequential basis. Control elements select the sample liquid delivered to each reaction vessel, select the reagents added thereto, and select the data processing for the photometer or other measurement information secured for reactants in that reaction vessel. The photometer elements apply and detect optical energy along selected directions to provide any of several photometric measurements, including for example of colorimetry, fluorometry, or nephelometry.

12 Claims, 12 Drawing Figures

AUTOMATED MULTIPLE-PURPOSE CHEMICAL-ANALYSIS APPARATUS

BACKGROUND

Analytical procedures carried out in clinical laboratories have, over the past decades, been automated to varying degrees in order, among other reasons, to increase productivity and to reduce human error.

Blood analysis, in particular, has benefited significantly from applying automation to those procedures. Today, many test procedures can be performed routinely on a given blood sample with great economy and reliability.

Typically the instrumentation dominating the field is based on the mechanization of the various procedural steps which previously have been performed manually by clinical technicians. Since these proven procedures are of the wet category, the instruments are involved in manipulating a variety of sample and reagent liquids, including mixing, incubating and taking measurements of the liquids. Beyond the operations directly involved in causing and in controlling the various chemical reactions, such instruments perform peripheral support activities, as for example washing and drying reaction vessels and fluid metering probes, maintaining reagent fluids at correct conditions to ensure reasonable stability, monitoring the chemical processes to eliminate errors, and analyzing and collating the resulting test data.

While the chemical procedures performed in such instruments often are relatively well established, the instruments frequently become complex as their throughput and their library of tests increase. A typical test protocol with various options includes the steps of introducing an aliquot of the sample liquid, adding reagent(s), mixing, if needed adding further reagent(s), incubating, and measuring reaction product(s). The measurement typically is a form of photometry such as colorimetry, fluorometry, nephelometry, or flame photometry; although other measurements such as spectroscopy can be used. A diversity of analytical hardware is commercially available, with each type specifically designed to meet the needs of a particular segment of the clinical laboratory community. This community can be divided into a number of distinct groups each having diverse needs. Large commercial clinical labs and clinical labs in large hospitals are the typical users of large analyzers capable of carrying out fifteen to thirty simultaneous tests on a single patient at rates of sixty to one hundred and twenty patients per hour. Such instruments usually incorporate a number of parallel test-dedicated channels, each capable of the operations recited above. Thus a ten-test instrument in this large instrument category would consist of such elements as a sample-introducing and distributing mechanism feeding each of ten separate reaction channels, and a reagent supply and delivery mechanism selectively feeding the ten channels. An analytical unit, typically with a separate measuring device for each channel, examines reaction product from each channel. Finally, a data collection and processing unit prepares an output report of the results determined in each channel for each sample fed to the system. Such instruments are costly and require a specialized support team. This makes such instruments economically justifiable only in an environment where the work load matches the relatively large capacity.

A variety of smaller instruments is available to smaller laboratories, and each is specific in its capability and features. Also, many suffer from operational deficiencies. In particular, single or dual channel bench-top analyzers are test-dedicated, relatively inexpensive instruments that can perform one or two tests at a moderate throughput. Typical tests are glucose and blood urea nitrogen, since they are popular and have clinical significance in combination. Samples are introduced manually, and an operator must transcribe displayed results.

Enzyme analyses are increasingly common in clinical laboratories, and this gives rise to different instruments each capable of performing one different class of tests. The requirement of enzyme-testing instruments is that reaction rates are measured during a time span, while the test fuid is maintained at 37° C. To measure the rate of reaction, the instruments either observe the reaction continuously, or look at the reaction progress at time intervals. In general, enzyme instruments rely on extensive manual activities to introduce sample and reagents. In some instruments reagent packs are loaded into the instrument and reagent is delivered from them to the reaction vessel by pushing an appropriate reagent-selecting button. Other instruments have a single reagent capability and require reagent changeover between tests. These instruments generally perform one test at a time. Due to the fact that the observation of reaction rate requires considerable time, the throughput is relatively low, e.g. thirty to fifty tests per hour.

Emergency conditions often require that a patient be tested quickly to determine the course of treatment. This requires instrumentation which can be maintained in a standby mode, where it is ready to perform a variety of tests in a relatively short time. To fill this need, stat analyzers are provded. These instruments commonly rely on the introduction of prepackaged reagent capsules which are sequentially ordered with patient samples, in a single channel instrument, to perform the prescribed tests. Here, many of the reagent delivery processes, which are performed automatically within the large automated instruments, are done outside the analyzer. In many instances, as in the du Pont ACA apparatus, the reagent-containing packages also serve as reaction vessels and as photomertic cuvettes. Thus other chemistry-specific hardware requirements, beyond just reagents, are supplied in disposable form to the instrument.

Another class of analytical hardware, developed at Oak Ridge and commercially produced by Union Carbide, Electro-Nuclenoics and American Instrument Corp., utilizes a centrifugal disc in which previously loaded sample and reagent liquids are centrifugally mixed and moved into a cuvette compartment. Continued rotation of the disc allows a stationary detector to observe the reaction product of each of a number of patient samples as the cuvettes rotate by the detector. This type of instrument is commonly classified as a form of batch processing device, since a single test is performed on the patient samples within a single rotor. The sample fluid and reagent are loaded into the rotor disc either manually or via a fluid dispensing accessory unit off the analyzer. The analyzer thus serves as a mixing, incubation and readout/data processor device. The batch nature of the process presents a number of logistical data collating problems. Results for a patient requiring a battery of tests are not available until that number of test batches is processed. While computer oriented solutions to the logistics are available in the form of accessories, they nevertheless cannot resolve the fundamental deficiency of a long wait for a complete battery of tests.

Thus, the basic instrument unit known in the art is a single fluid-delivery/chemical-processing/readout channel. Large instruments utilize a number of such test-dedicated channels in parallel to achieve operational objectives. Smaller, single-channel instruments perform test-specific operations either manually outside the instrument or by the introduction of already-formulated test-specific disposable packages. Such solutions, while producing less costly instruments and hence affordable by smaller laboratories, require a heavier human involvement in the operation of the instrument or a higher per test cost as a result of prepackaged reagents and/or disposables, compounded by the fact that the laboratory is generally limited to a single source for such materials.

OBJECTS

An analytical instrument is described here which, among others, has application in the determination of constituents in biological fluids such as serum, whole blood, urine etc. A primary object of the instrument is to provide a device of minimal electromechanical elements which is capable of performing a variety of test procedures automatically without extensive operator intervention. Such universality in test capability has heretofore been available only in large instrument systems where parallel, test-dedicated channels, each configured to perform a specific test procedure, are combined to achieve broad testing capability. Smaller analytical devices typically either require extensive operator involvement in configuring the system for a specific test, or rely on the performance of the steps unique to each specific test outside the instrument, often through auxiliary devices or the use of prepackaged test-specific modules. The known Centrifugal Analyzer System is an example of the former apparatus and requires that fluid addition to a reaction container be done outside the analyzer. The analytical system serves primarily to measure the results of the chemical reactions. An example of the latter apparatus is the ACA Analyzer System of E. I. du Pont de Nemours & Co. where modules containing test-specific reagent fluids and appropriate cuvette conditions are introduced to the instrument manually. The reagent fluids are transported through the instrument, after addition of patient sample fluid, through various universal mixing, incubation and photometric stations to develop the chemical reaction results.

Other prior art chemical analyzers include those marketed by Technicon Corporation, New York; the Mecoab instrument manufactured in the United Kingdom, the Robot-Chemist instrument of the Warner-Chilcott Company, the C-4 instrument of Perkin-Elmer Corporation; and the DSA-560 instrument of Beckman Instruments, Inc.

An objective of the instrument described here is to provide the capability, based on chemical protocols stored in the system, of varying the sample intake volume, adding if necessary a variable amount of diluent to the sample, providing one or several reagents in variable amounts, and adding diluent to the sample/reagent mix as required.

Continuous or repetitive scanning of the reaction vessels by a photometric system within the instrument produces a series of data points for each test in progress. These test points, with appropriate mathematical manipulation, are capable of providing end point and rate reaction constituent determinations for the samples.

In another embodiment of the invention, two or more stationary photometer systems can be situated along the path of the reaction vessels to intercept the various reactions in progress within the instrument and to obtain one or several measurements of the reaction progress at different times, as required to quantize the constituent concentrations. A third embodiment utilizes one or more stationary photometer units to which reaction vessels are moved for the duration of the observation cycle. In this case, the total observational time is of long continuous duration, while in the previous alternatives the total observation is the sum of intermittent measurements taken while the reaction vessels cyclically advance through the analytical system.

These and other alternatives, optionally available with this invention, for taking measurements o constituents in the fluid samples, represent preferred embodiments for specific economic situations. The first embodiment represents a sophisticated capability with high throughput potential in return for high mechanical complexity. The last embodiment on the other hand provides mechanical simplicity and economy, but with comparative reduction in the instrument processing rate capability. Thus each embodiment of the invention represents a preferred scheme for a definite range of instrument cost and productivity, but the choice of the photometric system does not affect the merits of the total instrument concept.

Another object of this invention is to enable the system, on demand, to increase or to diminish the amount of sample dilution in cases of abnormally high or low fluid constituent concentrations; such concentrations may fall outside the normal observational range of the photometer.

A further object of this invention is to permit the storage, in the instrument, of concentrated reagents whose formulation is optimized to maximize reagent potency life, minimize reagent transportation costs by reducing bulk being shipped, minimize reagent preparative activites, and/or reduce the reagent storage requirements.

In addition to the foregoing advantages, the sample and reagent dilution capabilities of instruments according to the invention provide a simple wash means for the sample and the reagent transfer devices. Further, a built-in thermal control element integral with each fluid transfer system allows preheating of the diluents prior to delivery, so as to achieve proper reactant temperature level rapidly in the instrument. The dilutional capability of the sample and the reagent fluids also increases the precision of these devices insofar as residual fluids, which are part of the metered fluid quantum and which in other instruments are washed and disposed to waste, remain part of the fluid quantity used in the reaction process.

Another object of the invention is to provide the ability for the analytical system to select automatically on command from memorized chemical protocols one or several reagents for delivery to the sample from a series of reagent containers within the instrument. The reagent containers can be selectively advanced into alignment with respect to one or more reagent transfer devices.

Thus the invention includes the flexible capability for a few transfer devices to deliver any available reagent, in any quantity within the delivery range of the transfer device, and further to add diluent to the sample/reagent mix in any quantity within the range of such device. Further, as the diluent is delivered it can be passed through a heating device to preheat the delivered fluid.

Another object of this invention is to provide an instrument of the above character with stat capability, i.e. the ability to be maintained in a standby mode to perform emergency tests with a minimum of preliminary conditiong. The achievement of this capability includes the following criteria: the instrument is to be capable of performing the specified tests with minimal delay; the incubation temperature level is to be maintained while the instrument is in standby; reagents are not to suffer from error-producing degradation of reactivity while the instrument is idle; and the electrical signal-processing devices that convert colorimetric observations into constituent concentration data are to be stable, or at least readily and preferably automatically correctable for drift and other deficiencies.

The present invention provides instruments that satisfy these and other requisites of a stat instrument, based on the following considerations. The instrument is in principle stat oriented and can be maintained economically in a power-on standby mode because it is a small, inexpensive, single process channel system with the capability of sequentially performing multiple tests on request. In this standby condition, all mechanical devices are inoperative. Electronic elements that require long warmup/stabilization time and computer hardware are maintained in the power-on mode. Incubation temperature maintenance, which is shared by diluent preheat and environmental control within the instrument, is partially off (diluent preheat having quick response capability is off until a test is requested). Reagent degradation is minimal since there is no reagent residing in transfer plumbing. All reagents are maintained in their respective containers on an indexable platform within a refrigerated compartment. The reagent transfer system picks up a small quantity of a reagent from the container and promptly delivers it to the reaction vessel. Thus reagent stability is maintained essentially at the useful container life at reduced temperature.

Since one or only few photometric devices are used for taking reaction measurements for all tests, (unlike large parallel channel instruments where a photometer is dedicated for each test procedure), it is economically feasible to introduce the sophistication to ensure the system integrity without making the whole instrument prohibitively expensive. Stability and general system reliability therefore receive appropriate attention.

It is also an object of this invention to provide an improved instrument for measuring fluid constituent concentrations by observing a plurality of physical characteristics which the sample fluid manifests. These characteristics of a given fluid sample can be observed singly or in combination as demanded by the chemical processes used to create a condition whereby a given fluid constituent concentration can be uniquely related to the fluid characteristic being measured. In this regard, it is an object of this invention to provide a combination of devices which enable measurements of light absorption by the test fluid to be made at a specific light frequency on a substantially continuous basis. It is also an object of this invention to provide, within the same detection system, means for making turbidimetric determinations, where light scattering due to solid matter in the fluid measured.

Additionally, an object of this invention is to provide the capability of making fluorescence measurements on fluid samples. Here the secondary light emission, resulting from the exposure of the fluid to ultraviolet light, is measured.

It is thus an object of this invention to provide a photometric detection system within a single instrument which can selectively take densitometric measurements at single or multiple light wavelengths, take nephelometric measurements, or take fluorometric measurements, as required by specific tests. All such measurements can be repeatedly made again and again while the test fluid remains in the analytical system, to acquire information relatable to the fluid constituent concentration on the basis of reaction rate.

It is also an object of this invention to provide the ability in an instrument of the above character to acquire information on the condition of the test fluid and/or reagent by taking measurements of the combined sample aliquot and reagent immediately subsequent to such combination process but prior to the initiation of chemical reactions.

Other objects of the invention will in part be obvious and will in part appear hereinafter.

GENERAL DESCRIPTION

This invention answers the needs of the smaller laboratory without compromising its efficiency or its access to state-of-the art technology, by providing the following instrumental system. Beyond resolving the problems associated with smaller instruments currently available, the system provides unique advantages as discussed herein. The new instrument, in its simplest configuration, has a single processing channel, a reagent supply, a readout unit, a control device, and is supported with fluid transfer devices. All subsystems provide the requirements of various specific test procedures. The instrument can operate as a fully automatic, discrete, sequential test, single channel, microanalyzer. Metered portions of each patient sample are picked up, in appropriate quantity as required by the test to be performed, and each is delivered to a reaction vessel in the instrument. The reaction vessel advances in the instrument, and appropriate reagent(s) is added in required volume(s). As the reaction vessel advances further through the instrument, it is scanned substantially continually by a mobile photometer system to obtain a series of data points which are used to determine the concentration of the constituent being measured by the test.

When a patient requires a number of tests, the control element of the instrument commands it to draw, in sequence, one sample portion for each test into a separate reaction vessel. The control element keeps track of each reaction vessel and directs that specific reagents be added to each in prescribed volume. The control element also specifies the wavelength of the optical filter required to make the appropriate photometric observation, and at the completion of the operations for each patient test it collates the results from the several portions and prints them out. Thus the instrument consists of an indexable reaction vessel/cuvette conveyor around which fluid metering modules are disposed. Each such module has sufficient flexibility to handle volumes required by any of the tests for which the instrument might be programmed. Thus any of a wide variety of test procedures can be performed on demand. Further, the scanning photometer provides a quasi-continuous screening of each test for the entire duration of the reaction at conditions specified for that test.

More particularly, an instrument embodying this invention typically has a conveyor mechanism which carries sample liquids in a single channel of separate containers in incremental fashion past various positions where reagents are added and measurements are made. Devices to deliver the sample, add reagent, add diluent, and take measurements on the reaction product to obtain the determination of the constituent matter in the fluid, are controlled to meet the requirements of the constituent-manifesting chemical reaction being carried out in each reaction container. Each successive reaction container being carried along the conveyor mechanism can thus perform a different constituent determination. The instrument embodying this invention will thus carry out multiple tests, in sequence, on sample portions in discrete containers.

Typically, in each operating cycle, which is defined as the time between reaction container incremental advances, the instrument performs the following functions. A sample transfer device picks up a specified volume of sample liquid based on the requirements of the test to be performed and delivers the portion to an empty reaction vessel on the conveyor. The sampler can, if necessary, also deliver a selected volume of diluent. At one or several subsequent positions along the conveyor, reagent transfer devices pick up reagents selected according to the chemical test requirements, from reaction containers in position at the reagent delivery stations, and deliver specified volumes of such reagents to the aliquots in the reaction vessels. Diluent is also added in required quantities.

Beyond the reagent delivery stations, optical windows provided on the reaction vessels are scanned by a colorimeter detector. The scanning rate of this colorimeter is such that all reaction vessels are observed during each operating cycle. Thus multiple observations are obtained of each aliquot through the whole reaction process. Rate measurements can consequently be carried out, as well as end-point tests.

The invention in this embodiment hence provides an instrument with the following unique combination of capabilities: minimal mechanical complexity for performing any chemical test procedure automatically, the test procedures can be carried out concurrently on portions from a number of samples, each sample can be analyzed for a number of fluid constituents by directing the instrument as to which tests are to be performed, and the continuous scanning of reacting aliquots allows the observation of the complete reaction process thus ensuring complete measurement and that samples with abnormal constituent levels are noted. Further, the ability to dilute reagent in the reaction vessel permits the storage of concentrated reagents, with additional advantages. One is that concentrated reagents, as shipped, do not have to be manually diluted before loading into the instrument. Another is that the size of the reagent storage compartment in the instrument can be small. Also, the stability of many reagents is improved keeping them in concentrated form.

The invention accordingly comprises the features of construction, combinations of elements, and arrangement of parts exemplified in the constructions hereinafter set forth, and the scope of the invention is indicated in the claims.

DESCRIPTION OF DRAWINGS

For a fuller understanding of the nature and objects of the invention, reference should be had to the following detailed description taken in conjunction with the accompanying drawings, in which:

FIG. 3A is perspective view, partly broken away, of a portion of the photometer for the instrument of FIG. 1.

DESCRIPTION OF ILLUSTRATED EMBODIMENTS

Figure 1:
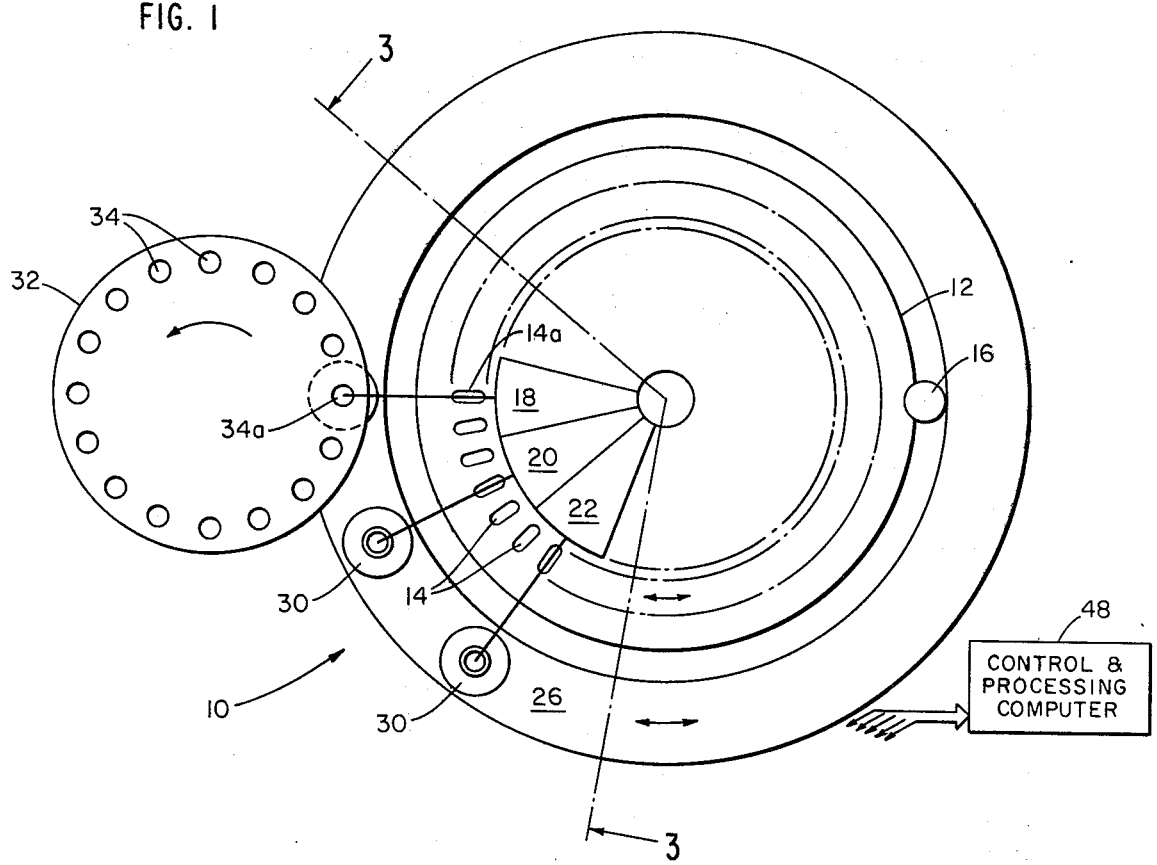
FIG. 1 shows an analytical instrument, partly in plan view and partly in schematic block form, embodying features of the invention.
Figure 2:
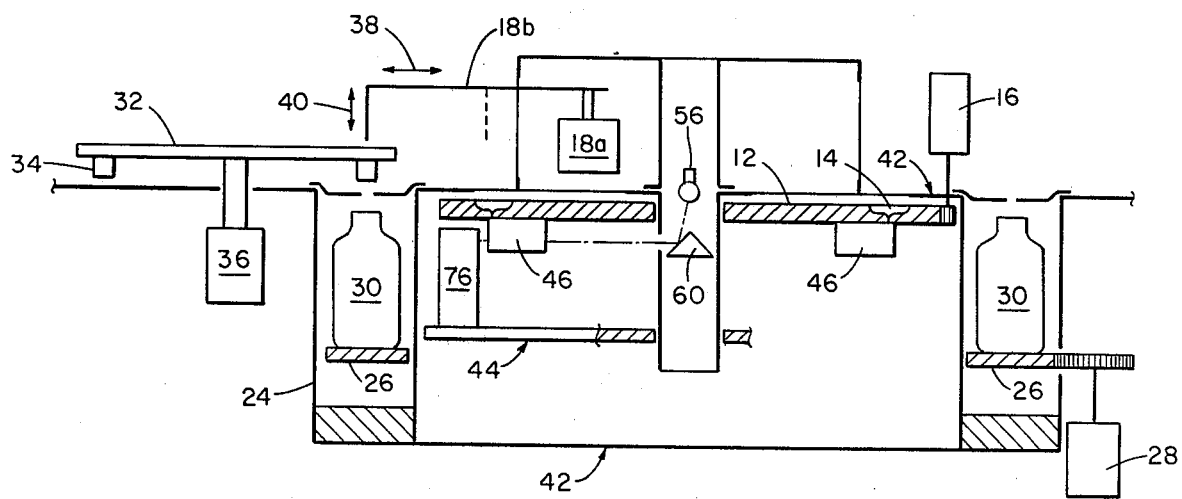
FIG. 2 is an elevation view, partly in section, of elements of the instrument of FIG. 1.

FIGS. 1 and 2 show a compact arrangement of major functional elements of an analytical instrument 10 according to the invention. A rotatable disc 12 carries reaction vessels 14 into which sample, reagent and diluent are introduced. The reaction vessels are arranged side-by-side at even angular intervals along a circular path and each has a longitudinal axis which is oriented radially. The disc 12 is mechanically linked to a drive motor 16 (e.g. with a rim drive) which incrementally rotates the disc. This advance brings each vessel 14 into successive alignment with each of several stationary fluid transfer devices, of which three designated 18, 20 and 22 are shown. The illustrated fluid transfer devices are located above the disc 12 side-by-side with one another at different radial positions, and hence are disposed above the reaction vessels 14 on the disc 12.

Radially outward from the disc 12 is a stationary annular compartment 24 which houses a rotatable annular platform 26, driven by a motor 28, and which carries reagent containers 30. Incremental rotation of the platform 26 brings different reagent containers 30 one-by-one into alignment with the fluid-transfer devices 20 and 22, which are designated for reagent delivery.

Figure 8:
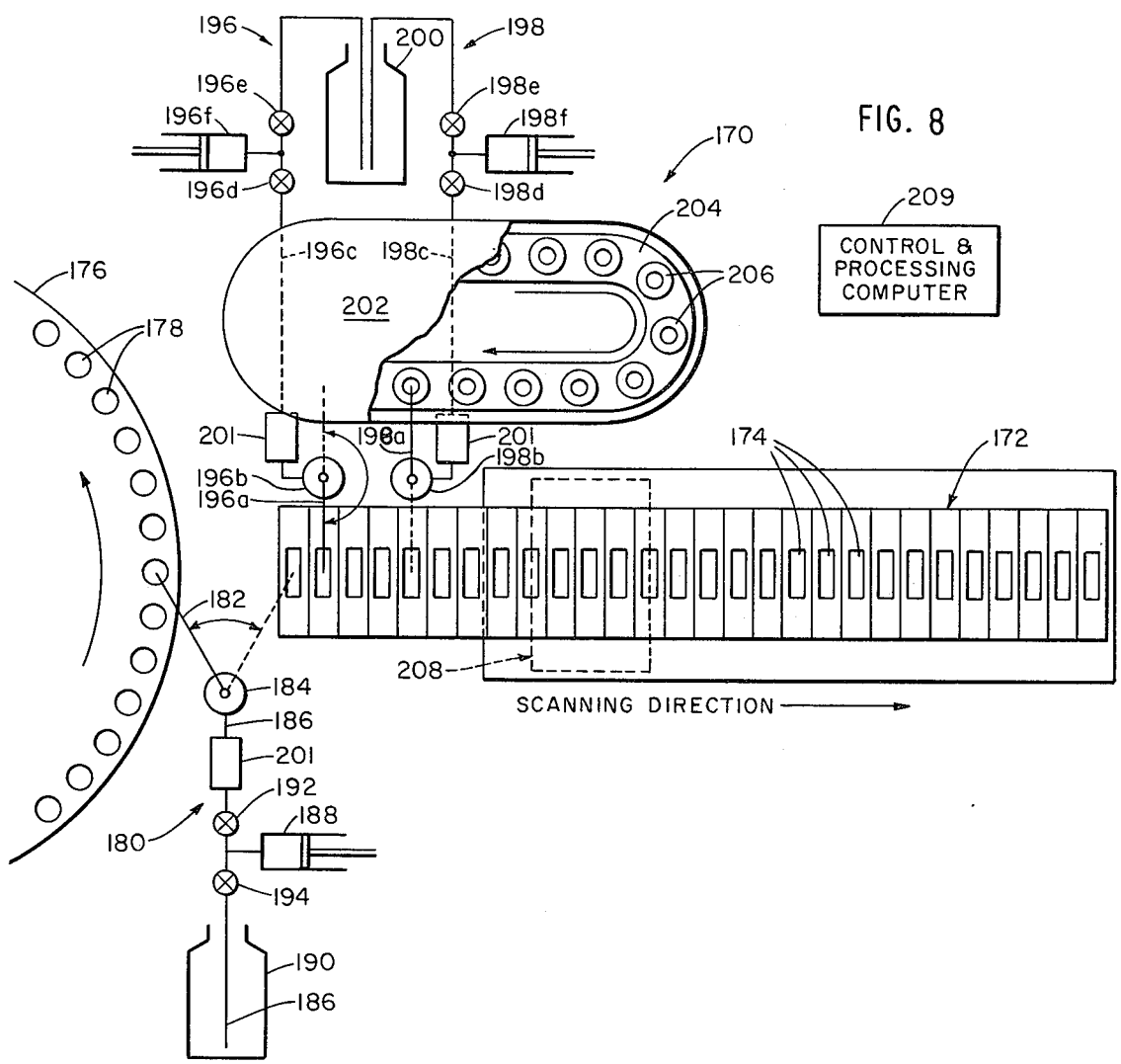
FIG. 8 shows another embodiment of an analytical instrument embodying features of the invention.

FIGS. 1 and 2 also show a removable sample tray 32, which carries sample fluid cups 34, mounted for driven rotation by a motor 36. The sample tray is driven incrementally to align the sample cups one-by-one with the probe of the transfer device 18, which provides sample transfer. Thus, with reference to the plan view of FIG. 1, both the reaction vessel 14a on the disc 12 and the sample cup 34a on the tray 32 are in alignment, for the transfer of sample liquid from the cup 34a to the vessel 14a, by the device 18. Subsequent incremental advance of the disc 12 brings the same vessel 14a, now containing a liquid sample, into alignment with the first reagent-transferring device 20. The transfer device 20 can transfer reagent or diluent from a container 30 aligned on the platform 26 with that transfer device to a reaction vessel. This operation can be repeated at other stations, e.g. when a reaction vessel 14 is incremented to be in alignment with the transfer device 22, to receive additional reagent and/or diluent. An alternative described with reference to FIG. 8 is to supply diluent to selected ones of the transfer devices, from a source other than the platform-carried containers 30, for delivery to reaction vessels 14.

The sample transfer device 18, typical of the other transfer devices 20 and 22, has a drive unit 18a which mounts a probe-carrying arm 18b. The drive unit responds to applied electrical signals to extend the arm 18b radially outward and conversely retract it, as designated with arrow 38 in FIG. 2, and to raise and conversely lower the arm as designated with arrow 40. The transfer device typically starts an operating cycle from a position where the probe arm is raised and retracted, and first extends the arm to the position shown with solid lines in FIG. 2. The arm is then lowered to introduce the probe into a sample cup 34, and the drive unit aspirates a selected measured volume of liquid into the probe. The probe is then raised, retracted to the position shown in FIG. 2 with dashed lines, where it is over a reaction vessel 14. The operating cycle continues with lowering of the probe and discharge of the aspirated liquid into a reaction vessel.

Where the liquid being transferred is to be mixed with liquid already in the reaction vessel, a vibrator such as a piezoelectric crystal or the like can be mounted on the disc 12 adjacent each reaction vessel and electrically powered to vibrate the reaction vessel for mixing the liquids. For an alternative mixing operation, the transfer device discharges the liquid into the reaction vessel with sufficient velocity to mix with liquids already present. This mixing entry of liquid from the probe of the transfer device can be enhanced by angling the end of the probe and by providing it with a nozzle-like aperture to discharge the liquid in a stream angled relative to the reaction vessel in a manner to introduce a mixing flow or current within the vessel. These and other mixing devices can be further provided and operated in accordance with known skills. Mixing can also be provided by directing a jet or stream of air into the vessel 14, or with a suitable mixing implement; care being taken to cleanse any mixing implement that is actually introduced into the liquids.

With further reference to FIGS. 1 and 2, the instrument housing 42, which carries the compartment 24 and suspends the disc 12, also contains a photometer unit 44 for measuring reaction product produced in each reaction vessel. The photometer unit examines the reaction product in a cuvette element 46 associated with each reaction vessel 14. The instrument as shown in FIG. 1 also has a control and processing computer 48 for controlling the instrument operation according to whatever test or tests are to be performed on each sample in a sample cup on the tray 32. These, and other elements of the instrument omitted from FIGS. 1 and 2 for simplicity, are described further beginning with reference to FIG. 3 which shows that the rotatable disc 12 is mounted in a suspended fashion from a top plate 50 of the stationary housing 42 by way of a depending central hub. Bearings 54 facilitate rotation of the disc about the hub. The illustrated housing top plate 50 overlies the disc and has apertures which provide access to the reaction vessels 14. These apertures preferably are only at locations where transfer devices or other elements require access to the reaction vessels; the top plate otherwise is preferably solid or otherwise opaque to block stray light from the photometric measuring system.

The hub 50, illustrated as a hollow cylindrical element, has a central interior cavity in which a light source 56, an optical mirror 58, and a multi-faceted reflecting cone 60 are mounted. The optical arrangement is such that the mirror 58 directs light from the lamp 56 axially onto the prismatic multi-faceted face of the cone 60 to produce multiple radial light beams. The hub 52 mounts a multiplicity of lenses 62, each at a different radial locations and each in optical alignment with a different cuvette element 46. Thus the angular separation between the lenses 62 typically is coincident with the angular separation of the reaction vessels 14 and of the cuvette elements 46.

Figure 3:
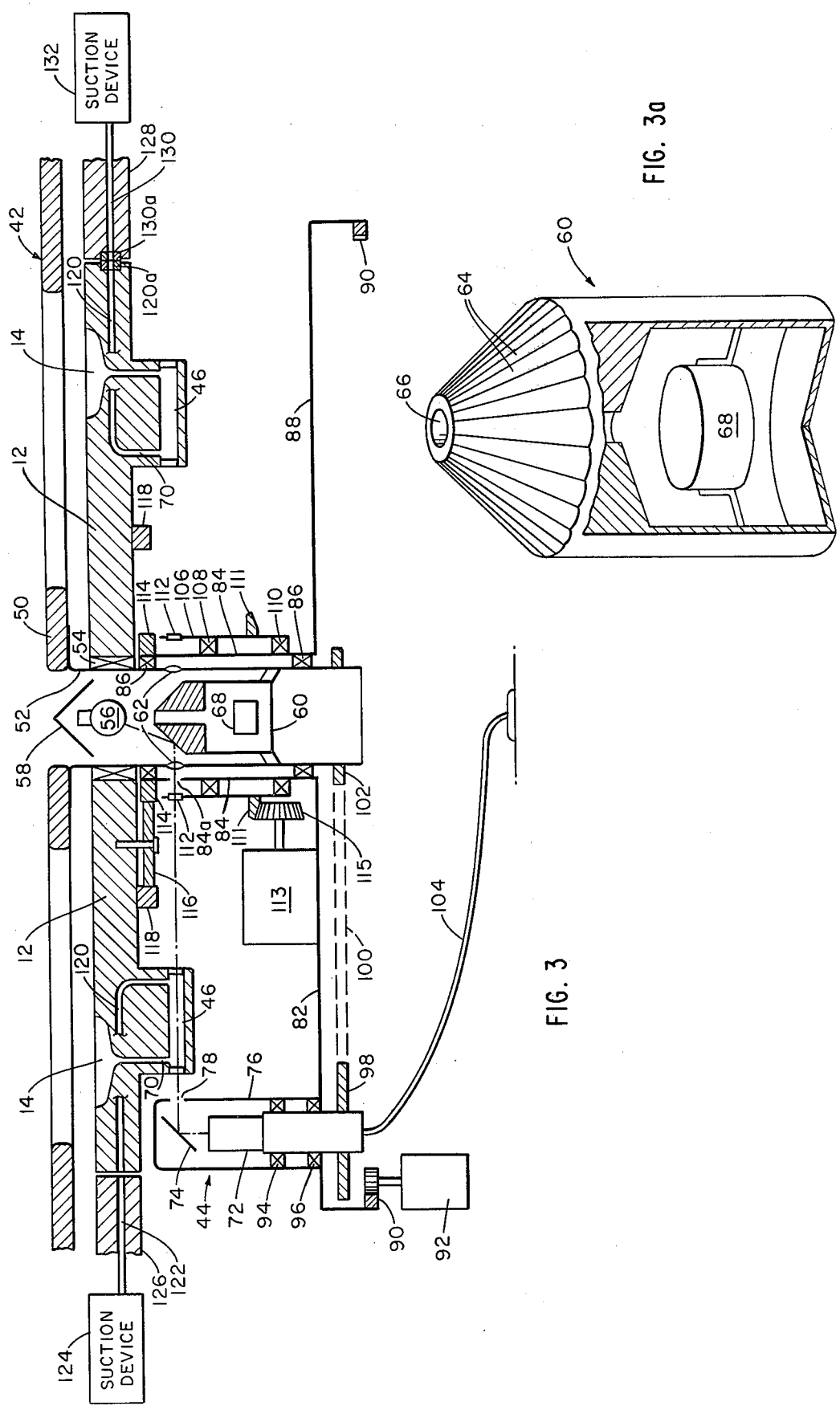
FIG. 3 is an elevation view in section along line 3—3 of FIG. 1 of elements of the FIG. 1 instrument showing further detail.

The multi-faceted prismatic cone 60 is shown in further detail in FIG. 3A. Optical faces 64, equal in number to the number of cuvette elements and correspondingly to the number of lenses 62 in the hub 52, form the conical surface of this element and are of mirror-like reflecting material. The conical portion is slightly truncated, however, and the apex is apertured with an optical window 66 which allows a portion of the source 56 light to enter the otherwise enclosed space within the cone. Within this space, a reference detector 68 is mounted to be concentric with the window 66 and hence in alignment through the window with the source 56. The cone 60, with the reference detector therein, is mounted in axial optical alignment with the source 56 and mirror 58 within the hub 52 by means of a bracket, as FIG. 3 shows.

Each reaction vessel 14 in the disc 12 is connected to a separate cuvette element 46 by means of a fluid conduit 70 in a manner described hereinafter. Each cuvette element has a horizontally and radially oriented longitudinal optical path therethrough as indicated in FIG. 3 with a broken line, and each is in radial alignment with a corresponding lens 62. Optical windows at each longitudinal end of each cuvette element allow light to pass axially along an optical path from a face of the prismatic cone 60 through a lens 62, the cuvette entrance window, the cuvette element 46, and the cuvette exit window. This optical path enters a light-shielding detector housing 76, which includes a measuring detector 72 and a reflector 74, through an orifice 78. The reflector 74 changes the radial light beam from the cuvette element to an axial beam directed to the measuring detector 72. The detector housing 76 is mounted on a rotatable arm 82. At its radially inner end the arm 82 joins and is integral with a sleeve 84 coaxially outside the hub 52 and rotatable therearound on bearings 86, 86.

The construction which FIG. 3 illustrates drives multiple elements with a single motor, in place of the motor 16 which FIGS. 1 and 2 show, and for this purpose provides the arm 82 as a radial member of a wheel structure 88 having a circumferential rim gear 90 engaged with a gear driven by a motor 92. Further, as also shown in FIG. 3, the measuring detector 72 extends parallel to the axis about which the disc 12 rotates, which is the optical axis of the source 56, and is mounted concentrically disposed within the housing 76 by means of bearings 94 and 96 which allow relative rotation. The base of the detector 72 extends below the wheel structure 88 and carries a sprocket gear 98 coupled by a chain or belt 100 to a further sprocket gear 102 fixed on the stationary hub 52.

With this arrangement, as the motor 92 drives the wheel structure 88 to rotate about the hub 52, the measuring detector 72 is successively moved into optical alignment with the light path which radially traverses each cuvette element 46. The measuring detector 72 is thus exposed to the optical energy output from each cuvette element. Further, the drive chain 100 revolves the measuring detector 72 within the housing 76 to maintain a fixed detector orientation for the purpose of keeping the electrical signal cable 104 output from the measuring detector from twisting. Thus, the measuring detector is carried in a circular path around the circular array of cuvette elements which the disc 12 carries, but at any given point around this circular path the same side of the detector is oriented north, due to the revolution which the chain 100 imparts to the detector 72 about the vertical axis which passes therethrough. The net result is that the cable 104 does not twist. The arrangement thus allows the signals which the measuring detector 72 produces to be applied to the control and processing computer 48 of FIG. 1 without the need of sliprings, brushes or other commutator-like sliding contacts that are likely to introduce error into the measuring signals. Notwithstanding the planetary motion of the measuring detector 72 which maintains the cable 104 in untwisted condition, the photometer housing 76 continually has the light orifice 78 directed radially inward toward the cuvette elements. A further feature of the illustrated construction is that the hub-encircling sleeve 84 has a single aperture 84a therein oriented to direct source illumination from the cone element 60 to a single cuvette element 46 at a time. This arrangement applies source illumination to only the single cuvette element 46 which is aligned with the measuring detector 72 at any time, and thereby eliminates stray light and interference problems.

As also shown in FIG. 3, a tubular filter holder 106 encircles sleeve 84 and is supported concentrically on the sleeve by bearings 108 and 110. The holder mounts optical filters 112 and is movable to align any one in the path of the measuring light between the sleeve aperture 84a and the photometer orifice 78. A conical ring gear 111 coupled to the filter holder 106 is mechanically linked to a motor 113 through a mating gear 115. The motor 113 can thus turn the filter holder 106 to align any selected filter 112 with the measuring light beam. By way of example, two alternative filter holder modes of operation can be provided. In one, the holder is driven at a constant rotational speed and, as the appropriate filter breaks the measuring light path, a photometer reading is made. Alternatively, the motor 113 steps the motor shaft in angular increments to interpose selected filters in the light beam. The FIG. 1 computer can provide this and other operations as detailed hereinbelow, based on instructions the computer memory stores for each test procedure.

FIG. 3 also shows one means of sychronizing the photometer motion described above with the rotational indexing of the disc 12. For this purpose, the sleeve 84 carries, at its axially upper end just below the disc 12, an interrupted ring gear 114. This gear engages a pinion gear 116 rotatably carried on the underside of the disc 12 and which is further engaged at its outer periphery with a ring gear 118 that is keyed to the disc 12. The gears are selected to drive the disc 12 by one indexing increment, i.e. the angular distance between adjacent reaction vessels 14 (which illustratively is the same as the angular distance between adjacent cuvette elements 46) while the photometer arm 82 and correspondingly the wheel structure 88 completes a full revolution. In this manner, the single motor 92 drives both the photometer mechanism and the disc 12, and the only further motors required are those which select the filters 112 and which turn the sample tray 32 (FIG. 1). Alternatively, independent motors for the disc 12 and for the photometer can be provided with synchronization through the electrical controls to the separate motors.

With continued reference to FIG. 3, the liquids in each reaction vessel 14 are transferred to the associated cuvette element 46 by way of the conduit 70 at the desired time, typically after sufficient mixing. This transfer is accomplished by providing a negative pressure within the cuvette element 46 by suction applied to a conduit 120. This conduit feeds out through the disc 12 from the cuvette element to the periphery of the disc, where it couples with a stationary further conduit 122 which feeds to a suction device 124, i.e. a source of sub-atmospheric pressure. Each conduit 70 and 120 is internal to the disc 12, whereas conduit 122 is within a disc-abutting arm 126. As the arm 126 is brought into intimate contact with the outer peripheral edge of disc 12 so that conduits 122 and 120 are aligned, the suction draws liquid from the reaction vessel 12 to the cuvette element 46. The suction is discontinued when the cuvette is filled, which can be controlled by limiting the time the suction is applied or by a detector which monitors the entry of liquid into the conduit 120.

As indicated schematically at the right side of FIG. 3, a further arm 128 carrying an evacuating conduit 130, is coupled with the outer edge of the disc 12, at a rotational position which the cuvette elements pass upon completion of the reaction and measuring operations. The opposed, facing ends 120a and 130a of conduits 120 and 130 are provided with snap-on and snap-off fluid couplings, or with releasable seals, to transfer liquid between the conduits. When the conduit ends are in sealing, fluid-transferring alignment, a suction device 132 coupled to the conduit 130 aspirates and thereby removes all liquid from the reaction vessel 14 and from the cuvette element 46. The reaction vessels and cuvette elements can be further cleansed by adding and scavenging wash liquid with further transfer devices and further suction devices coupled in the same manner.

Figure 4:
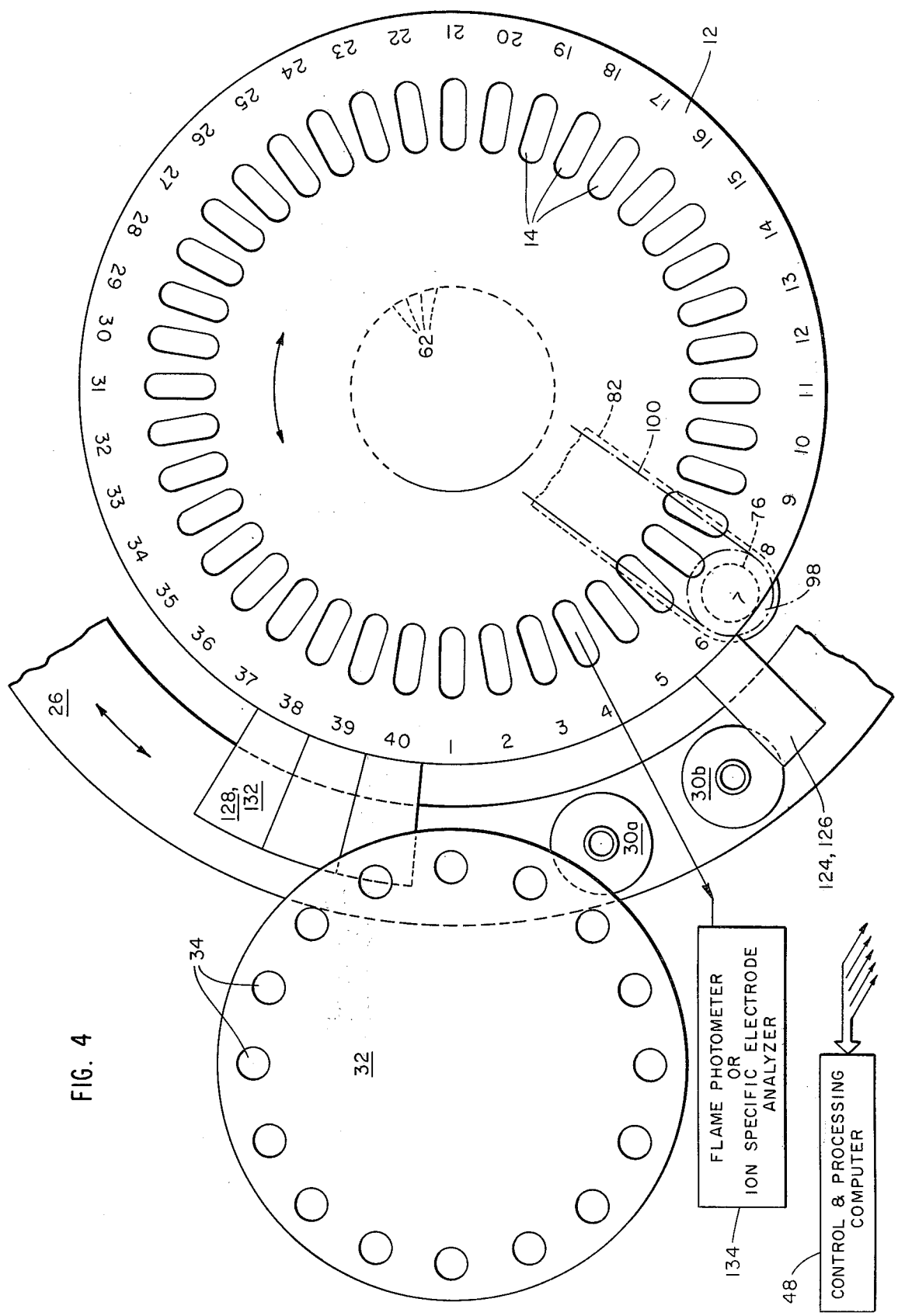
FIG. 4 is a view like FIG. 1 of a particular embodiment of an instrument according to the invention.

Further in accord with this invention, FIG. 4 shows the disc configuration for an analytical instrument of the type described above and having a disc index period of ten seconds and providing five minutes of incubation time. Here disc 12 has forty reaction vessels 14 numbered one through forty and evenly spaced nine degrees apart. The disc indexes nine degrees in every ten seconds. The initial positions (2) through (5) are illustrated as available for reagent addition. In the particular configuration shown, sample liquid is transferred from sample cup 34 to the vessel at position (1) and reagent can be added from reagent container 30a at position (3) and from container 30b at position (5). At position (6) a suction device 124 and arm 126 transfers the liquids from the reaction vessel to the cuvette element. Positions (7) through (37) are available for fluid incubation in the cuvette element and for photometric measurement. For this purpose, the hub is provided with a lens 62 at each of positions (7) through (37) and the photometer arm 82 revolves at a rate of one full revolution every ten seconds. Thus the cuvette element at each of positions (7) through (37) is photometrically measured once every ten seconds. Since the disc 12 contains forty cuvette positions, the observation time at each cuvette position where for example the cuvette cavity size of one-quarter of the spacing between adjacent cuvettes is 0.062 seconds (i.e. the observation time per cuvette element is ten seconds divided by forty positions, and divided further by one-quarter, or 0.062 seconds). Further, the time required for a given cuvette element to travel from position (7) to position (37) is thirty positions times ten seconds, or five minutes. Positions (38), (39) and (40) are available for emptying, washing and drying the reaction vessels and the cuvette elements. A suction arm 128 and suction device 132, or like cleansing device, as described with reference to FIG. 3 is provided at each of these positions.

The instrument of FIG. 4 can also perform nonphotometric tests, such as sodium and potassium determinations performed with ion-selective electrodes or by flame photometry. These tests are carried out by removing the liquids from the reaction vessel to a separate measuring device 134 after appropriate sample conditioning and incubation with reagents on the disc 12.

The system thus described with reference to FIG. 4 can perform three hundred sixty tests per hour. In a stat mode, the first test result can be available in less than ten minutes from presentation of the sample, and additional test results can be generated at ten second intervals. The analytical system of FIGS. 1–4 operates under control of a computer 48 which will now be described further.

A control and processing computer 48 for the instrument described with reference to FIGS. 1 through 4 can employ any of numerous coventional constructions and can be programmed with conventional skills as needed to provide operation in accordance with the invention. The computer typically has a keyboard for operator entry and interaction (i.e. interrogation), a cathode ray tube display, a printer for preparing records of measurement values and other output information, and an alarm device for reporting alarm conditions including out of limit measurements. In addition to these operator interface elements, the computer typically employs conventional processor elements including accumulators, buffers, shifft registers, timing and control logic, and memory elements, some of which provide permanent or hard-wire storage and others of which provide storage of program instructions and information entered via the keyboard.

Typical operation of the computer in cnjunction with the instrument 10 of FIG. 1 includes identifying each sample placed on the tray 32 and determining the analyses to be performed on that sample. This information can be entered into the computer via the keyboard, but more typically is entered automatically by machine-reading sample identification and test information from a label or tag associated with each sample cup 34. Thus, when the tray 32 is loaded with a series of sample cups 34, the computer stores—in a memory location assigned to each tray position—the identification of the patient from whom the sample in that position was obtained and the identification of the analysis to be performed on that sample, together with other pertinent information such as the physician or hospital to which results are to be reported, specific limit conditions, and the like. As each sample cup 34 advances to the position of sample transfer device 18, the computer controls the instrument to place sample in a separate reaction vessel, or set of one or more reaction vessels, as required for each analysis. During subsequent increments of the tray 12, the computer controls the selection, volume and dilution of reagents introduced to each reaction vessel, as well as the incremental position of the disc 12 at which each reagent and diluent are introduced, thereby controlling the sequence and relative timing of reagent addition(s). Each transfer device 18, 20, and 22 can include a heater (as illustrated in FIG. 8) to bring the liquid which it delivers to whatever elevated temperature is appropriate for each reaction.

Aside from controlling the introduction of liquid into each reaction vessel, the computer 48 controls the measurement of the resultant reaction and reaction product(s). Thus as the photometer unit scans by each cuvette element, the computer selects the optical filter 112 appropriate for measurement on that cuvette element, directs the storage of the resultant measurement data to the proper memory location, tests each measured value against selected limit values, and raises an alarm when an out-of-limit condition is sensed. The computer also controls the processing of the data accumulated for each reaction vessel from different scans, and arithmetically processes the multiple test points according to the algorithm appropriate for the test being conducted. In similar manner, the computer can transfer the reactants to a separate analysis device, such as the flame photometer or ion specific analyzer 134 shown in FIG. 4, for performing off-disc measurements. The cleansing of reaction vessels as illustrated in FIG. 4 at the tray index positions (38), (39) and (40) can also be controlled with the computer. The foregoing operations which the computer 48 provides are illustrative, and other and different arrangements and operations can be provided within the scope of the invention using the flexible hardware arrangement which the invention provides for an analytical instrument.

Figure 5:
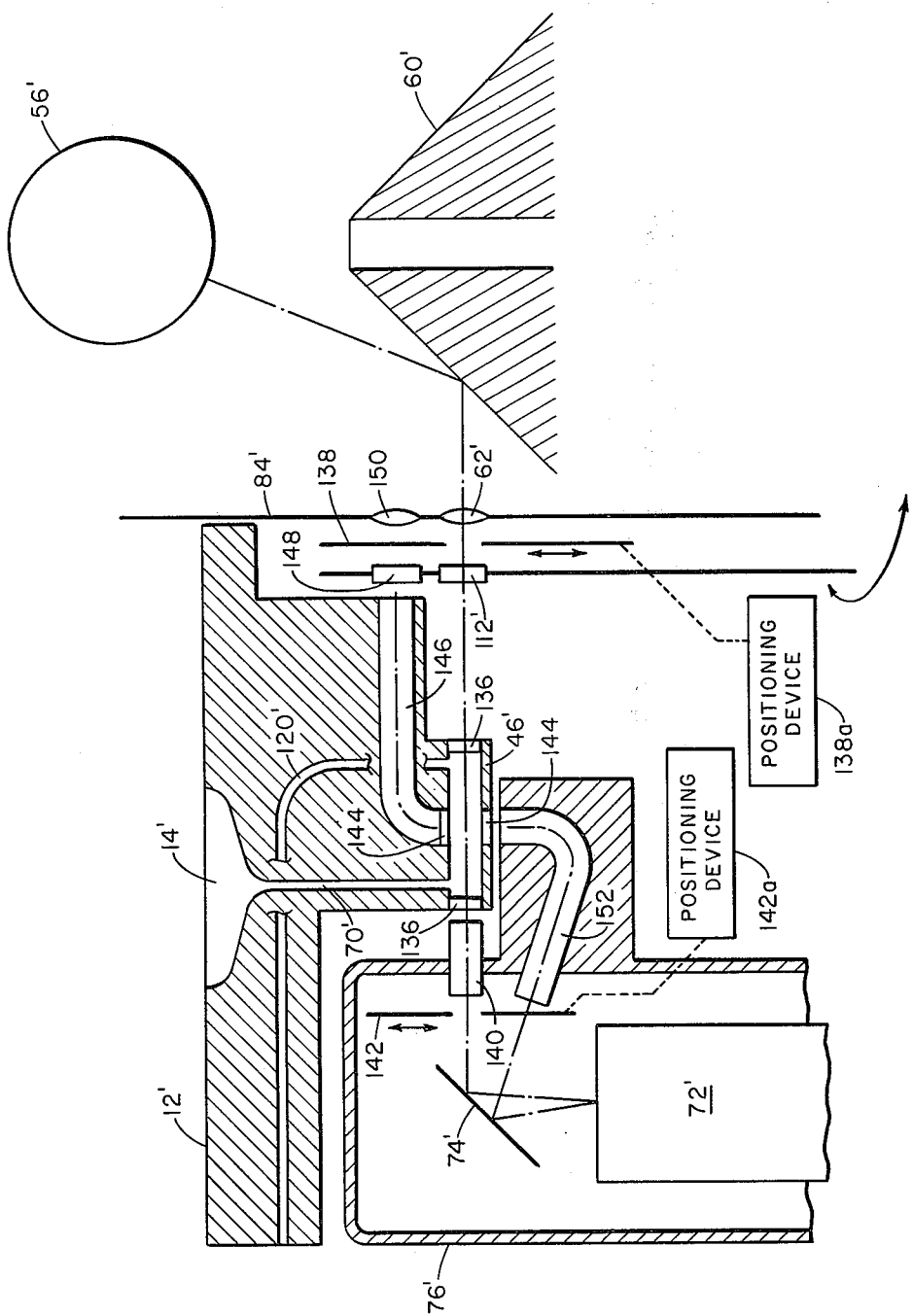
FIG. 5 is a fragmentary elevational view partly in section of further photometer structure in accordance with the invention.

FIG. 5 illustrates schematically an embodiment of the photometric system according to the invention capable of any one of several different photometric measurements, e.g. densitometric, nephelometric and fluorometric measurements, of the sample within a cuvette element. Elements in FIG. 5 which relate to corresponding elements in FIG. 1 bear the same reference numeral with the addition of a superscript prime. The cuvette element 46', situated within disc 12' and coupled to reaction vessel 14' by means of fluid conduit 70' and to a waste disposal or suction means by conduit 120', has two optical windows 136, 136, each at a longitudinal end of the cylindrical cuvette cavity. These windows and the longitudinal optical path through the cuvette element are in optical alignment with the path of light from the lamp 56' as reflected by the cone 60' and which passes successively through lens 62', the aperture in a source mask 138, a filter 112', and, on the exit side of the cuvette element, a light pipe 140 leading into the photometer housing 76'; the aperture in a detector mask 142, the photometer reflector 74', and eventually to the measuring detector 72'. This optical path corresponds to the photometer optical path described above with reference to FIG. 3.

FIG. 5 also shows that two additional optical windows 144, 144 are provided along the length of the cuvette cavity and oriented on an axis perpendicular to the longitudinal cuvette axis. The illustrated windows 144, 144 are opposite one another along this perpendicular axis. A further light pipe 146 is imbedded within the body of disc 12' and provides an optical path to the entry window 144 from the source provided by lamp 56' and cone 60' by way of a further filter element 148 and a further lens 150. The source mask 138 is shown in a position where it blocks this latter optical path. However, the mask not only is rotatable as described above with reference to the FIG. 3 mask 84', but is axially shiftable to align the aperture therein with either the lens 62' and the filter 112' as shown, or with the filter 148 and the lens 150. In the latter position, the source mask 138 blocks the path of source light longitudinal to the cuvette element and instead provides a path for source light to enter the cuvette element transversely, through the entry window 144. Thus the FIG. 5 arrangement provides two alternate and orthogonal paths for light from the lamp 56' to enter the cuvette element.

There likewise is a second optical path for light output from the cuvette to be applied to the measuring detector 72'. This second path employs a light pipe 152 mounted with the photometer housing 76' and which provides an optical path from the exit window 144 through the detector mask 142 and to the measuring detector 72' via the photometer reflector 74'. The detector mask 142 can be moved from the position shown to a second position where the aperture therein is aligned between the exit facet of optical pipe 152 and the reflector 74', for applying transversely exiting light from the cuvette element to the measuring detector while blocking the path of light output from along the axis of the cuvette element. Arrows in FIG. 5 show the two directions of movement for the source mask 138 and the one direction of movement for the detector mask 142; selective positioning devices 138a and 142a respond to signals from the FIG. 1 computer 48 to provide these motions. By way of specific example, the detector mask 142 can be driven by any of several positioning devices including a solenoid. Alternatively, the detector mask 142 can be rotatable to select either available path for light to enter the photometer housing 76'. The source mask 138 likewise can employ any of numerous constructions and motor/positioning devices.

The optical elements for the photometer construction of FIG. 5 are selected to transmit the range of wavelengths at which measurements are made, including, for example, both visible light and ultraviolet light in light pipe 146 and in the elements in the illuminating path it provides. It will also be noted with further reference to FIG. 5 that the output, detector light pipes 140 and 152 move with the photometer housing, whereas the cuvette element and light pipe 146 move with the rotatable disc 12'.

Figure 6A:
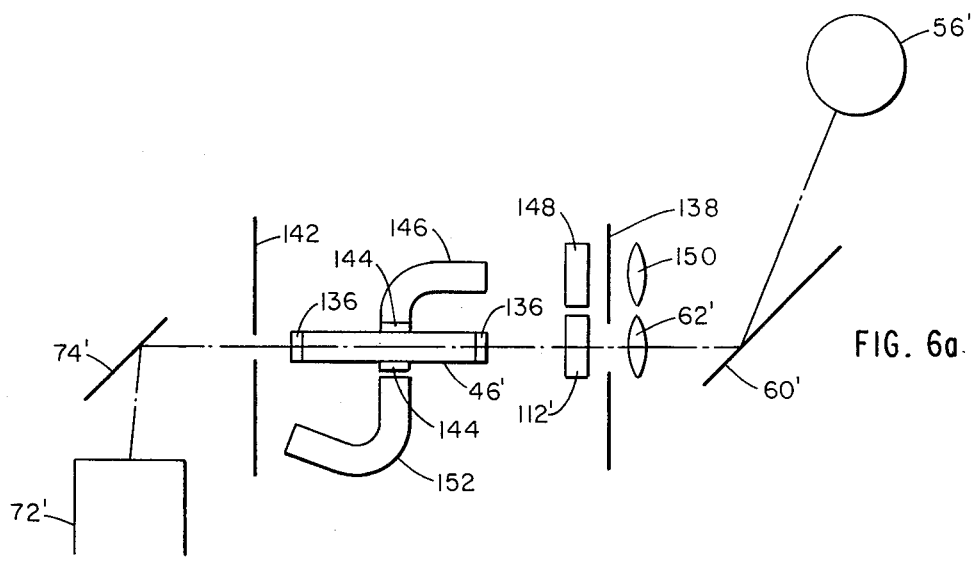
FIGS. 6A, 6B and 6C are simplified schematic representations showing different operating conditions of the FIG. 5 photometer arrangement.
Figure 6B:
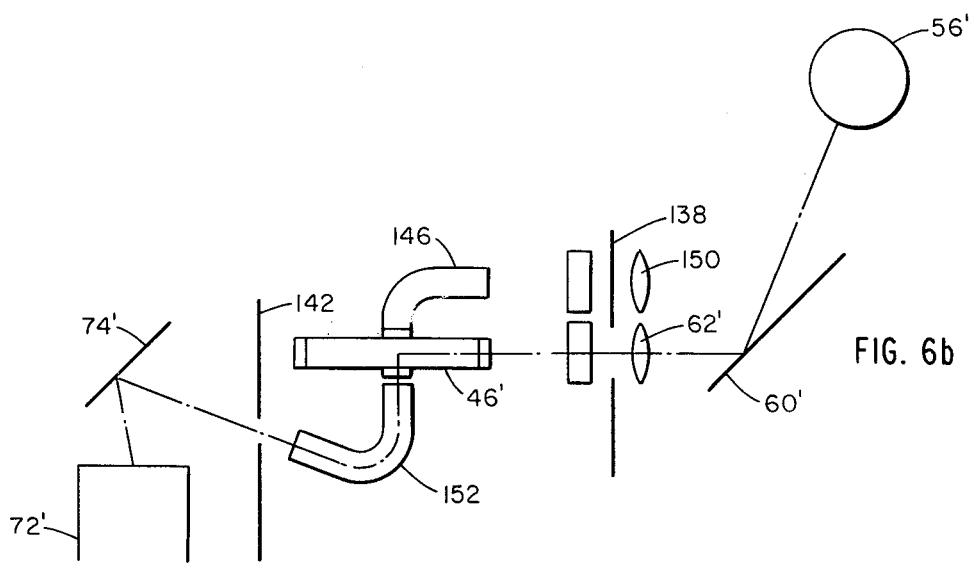
Figure 6C:
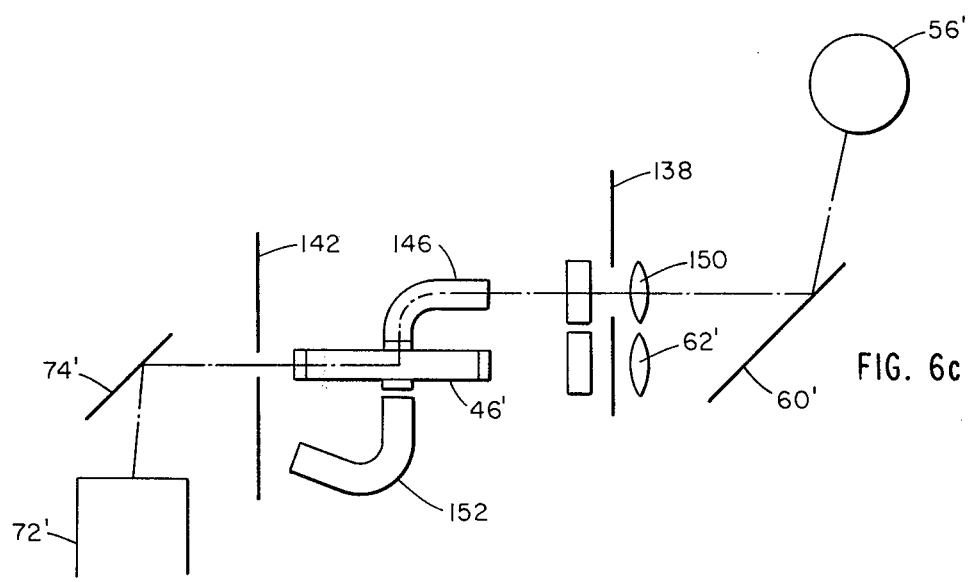

FIGS. 6A, 6B and 6C show three observational modes which the photometer construction of FIG. 5 provides. Elements in these figures bear the same reference numerals as in FIG. 5. FIG. 6A shows the mask 138 and mask 142 positioned to provide a light path along the longitudinal axis through the cuvette element as appropriate, for example, for performing a densitometric determination. The light traverses the lens 62', the aperture of mask 138, filter 112', and enters the cuvette element through entry window 136. Light from tthe cuvette exit window 136 passes through aperture of mask 142 and is directed by reflector 74' to the measuring detector 72'. The masks are positioned to block light from entering light pipe 146 and which exits from light pipe 152. Measurement of light-absorption characteristics of liquids within the cuvette element typically are made with this configuration.

FIG. 6B illustrates the condition where mask 138 provides for axial entry of source light into the cuvette element, whereas detector mask 142 is shifted to deliver scattered light to the detector 72'. This condition is used, for example, to perform a nephelometric measurement. The light applied to the detector 72' is dependent upon and hence is a measure of the diffusion due to solids in the liquid within the cuvette element. The masks block light from entering light pipe 146 and which exits from the cuvette window 136.

FIG. 6C shows the two masks 138 and 142 positioned to provide a fluorometric measurement. Here, light conditioned by lens 150 and filter 148 passes through mask 138 to light pipe 146 to enter the cuvette element through window 144, perpendicular to the longitudinal axis of the cuvette element. Light emerging axially from the cuvette element through the exit window 136 is passed by mask 142 to reflect from mirror 74' onto the detector 72'. Here incident ultraviolet light interacts with the fluid constituent of interest to cause fluorescence at a different wavelength, which in turn is measured to determine the concentration of the selected constituent.

The photometer arrangement of FIG. 5 is capable of a further, fourth, arrangement, i.e. entry of light to the cuvette element through light pipe 146 and exit of light via the opposite window 144 and light pipe 152. This condition, however, provides the same measurements as the FIG. 6A arrangement, and the latter is considered preferable because of the longer pathlength of light it provides through whatever liquids are being measured.

Figure 7:
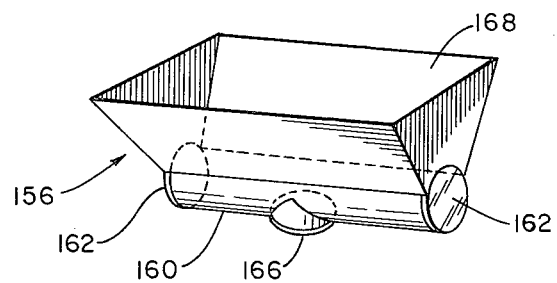
FIG. 7 is a perspective view of an alternative cuvette vessel.

FIG. 7 shows a cuvette device 156 which can be used for practicing the invention in place of the reaction vessel and cuvette element described above. This cuvette device 156 has a semicylindrical analysis chamber 160 with optical windows 162 at either longitudinal end and with a further optical window 164 located along the chamber length and facing transversely to the chamber longitudinal axis. This arrangement of optical windows 162, 162 and 164 with the analysis chamber 160 can be used in any of the measuring conditions described above with reference to FIGS. 5 and 6.

The FIG. 7 cuvette device 156 also has a trough portion 168 directly above and feeding into the analysis chamber for the receipt of sample, diluent, and reagent from the several transfer devices.

With this construction of a cuvette devices, the sample and all reagents are introduced directly to the cuvette chamber and are hence available for measurement immediately upon introduction; it will be appreciated that mixing of the liquids can be carried out, as by a liquid stream or an air stream directed into the analysis chamber through the opening which the trough portion provides. The cuvette device 156 can be constructed for permanent mounting to the instrument disc 12 (FIG. 1). Alternatively, it can be a single-used disposable element to provide an instrument with minimal requirements for cleaning between introduction of different samples.

The foregoing embodiments of the invention transport the reaction vessels and the cuvette elements along circular paths, and employ circular movement of the photometer detector to measure reaction product. The invention, however, can be practiced with other motions, as now illustrated with reference to FIG. 8, which shows an analysis instrument 170 in which a conveyor 172 carries cuvette vessels 174 along a closed path which has a straight section along which at least incubation and measurement occur. The conveyor 172 advances the cuvette vessels one-by-one with upright orientation along a straight, flat path from left to right in FIG. 8. The conveyor then inverts the vessels and moves them from right to left underneath the former path to begin again the upright forward advance. Each cuvette vessel can, for example, be constructed in the manner shown in FIG. 7, and can be washed for repeated use or be disposable and replaced.

A start end of the conveyer 172 (the left end in FIG. 8) is in close proximity to an indexable sample tray 176 which carries sample cups 178, each of which contains a liquid sample to be analyzed. A sample transfer system 180 is located to transfer sample from a tray-carried cup 178 to a cuvette vessel 174 at the start end of the conveyer 172. (Where desired, alternate sample cups on the tray 176 can contain a cleansing solution for washing the sample transfer probe after each sample-transferring operation; and this same operation can be used with embodiments described previously.) The illustrated transfer unit 180 includes a probe 182 mounted on a driven support 184. The support can move the probe vertically and rotationally to align the probe above a sample cup on the tray 176, lower the probe into the cup, raise the probe from the cup, and transfer the probe to the position shown in FIG. 8 with dashed lines over a cuvette vessel 174 for discharging the sample volume withdrawn from the cup 178 into the vessel. The transfer unit accomplishes the fluid aspiration and delivery by connecting the probe 182 via a conduit 186 with a variable stroke pump 188 and with a diluent container 190. A valve 192 is connected in the conduit 186 between the pump and the driven support 184 and another valve 194 is connected between the pump and the diluent supplying container 190. The valves determine the source and the destination of the displaced fluid as the pump is driven.

The sample transfer system 180 is initially filled or primed with diluent from container 190. With valve 192 open and valve 194 closed, retraction of the piston illustrated in pump 188 causes the system to aspirate sample from a sample cup 178. After transfer of the probe to a cuvette vessel 174, reversal of the pump operation discharges the aspirated sample volume. Continued operation of the pump 188 discharges diluent in whatever volume is appropriate for the test in process. Upon completion of this sample and diluent delivery, valve 192 closes and value 194 opens, and the pump piston is retracted to replenish the diluent supply within the transfer system. After the probe is cleaned, using any known practice, the transfer cycle is complete and ready to repeat. (Note that the discharge of diluent may clean the probe interior sufficiently.) The pump 186 is typically driven by a proportional motor, for example a stepping motor, and hence can meter out a range of liquid volumes in integer quantities of the smallest motor step.

After the specified volumes of sample liquid and of diluent, if any, are delivered to a cuvette vessel 174 at the start end of the conveyer 172, the conveyer advances to bring another cuvette vessel into the start position. Downstream from this position along the conveyer, i.e. to the right in FIG. 8, additional fluid transfer units, of which two units 196 and 198 are shown, are positioned for alignment with cuvette vessels at different conveyer locations. Each of these transfer units is functionally identical to the sample transfer unit 180. Thus the reagent transfer unit 196 has a probe 196A, a probe-driving support 196B, a conduit 196C, valves 196D and 196E, and a pump 196F. And the unit 198 is constructed similarly with elements 198A, 198B . . . 198F. A common supply 200 furnishes diluent to the two units.

Also, each transfer unit 180, 194 and 196 is illustrated as having a thermal block heater 201 thermally coupled with the conduit section which feeds from the pump to the driven support. The heater applies heat to the conduit and thereby heats liquid which the probe discharges. The temperature level at which the blocks are maintained is controlled and thereby the liquid within each conduit can be brought to a controlled level. The liquid being heated in the conduit typically is the diluent, which generally represents the larger of the two liquid volumes delivered by each transfer system. In this manner, the total fluid mix introduced into each cuvette vessel can be raised close to the desired reaction temperature. The last incremental step to bring the liquid in each cuvette vessel to the proper temperature can be provided by maintaining the whole conveyor device, or at least a portion of the upper flight of the conveyor 172, in an enclosure which contains a circulating atmosphere maintained at the selected temperature. Alternatively the conveyer can descend to lower the vessels into a water bath.

With continued reference to FIG. 8, the instrument 170 is further illustrated as having a refrigerated compartment 202 which houses reagents. The compartment is maintained at a low temperature, typically 4° to 6° Centigrade, to diminish reagent degradation. This storage of reagents in concentrated form and at low temperature, which the invention provides, allows the instrument to use many reagents in the same containers in which they are purchased, without dilution or other preparation. Further, it enhances long reagent life. A conveyor 204 within the compartment 202 carries the reagent containers 206 to position each container under a transfer system as needed for reagent transfer to the conveyed cuvette vessels 174.

Thus, in the embodiment which FIG. 8 shows, the first left-most cuvette vessel on the conveyer 172 is positioned to receive sample liquid by way of the sample transfer unit 180, the next vessel 174 is positioned to receive reagent by way of the transfer unit 196, and the fifth vessel along the conveyer 172 is positioned to receive reagent by way of the transfer unit 198. As the conveyer 172 advances the vessels in this manner, it carries the reaction vessels in stepwise fashion to a photometer assembly 208. Here the reaction progress in each cuvette vessel can be measured, typically as a change in optical density of the reactants.

Figure 9:
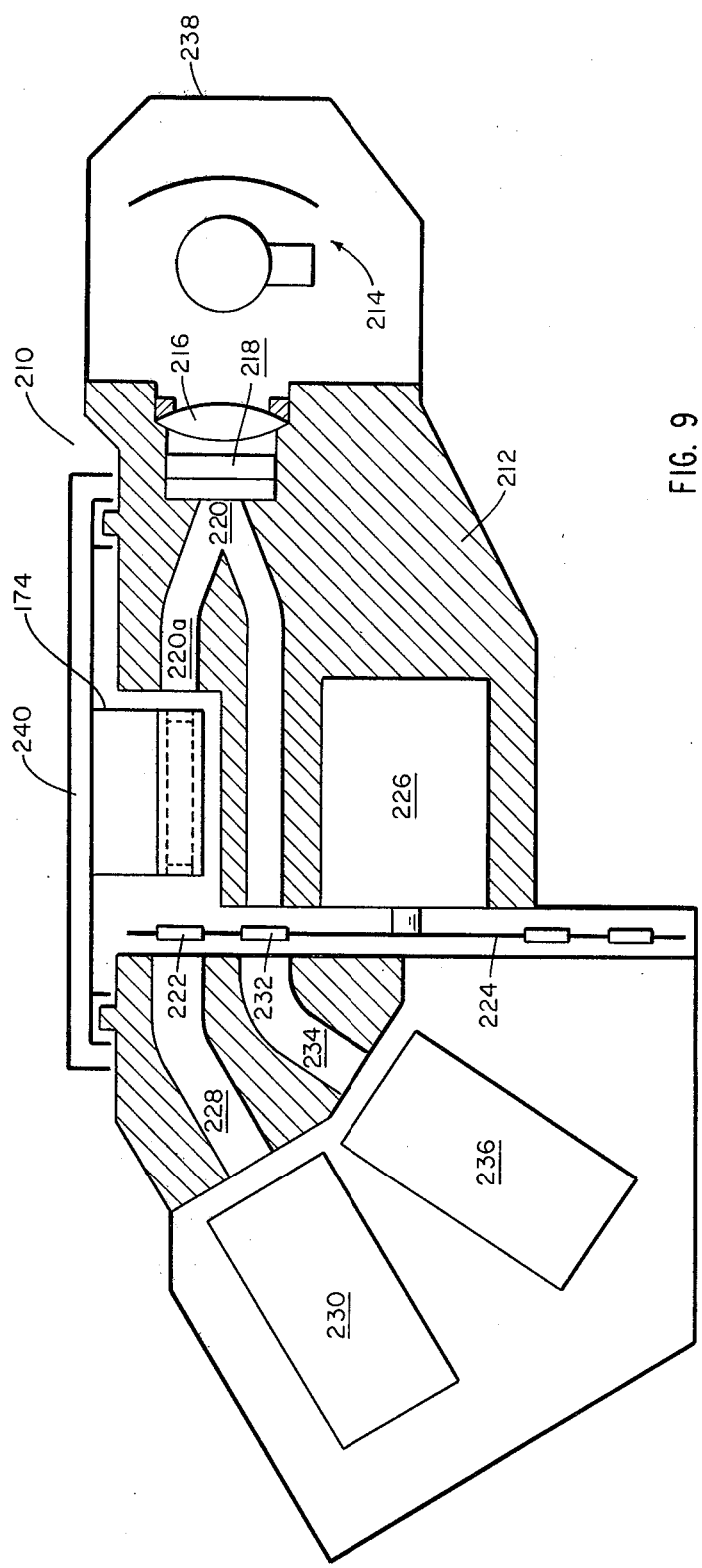
FIG. 9 is an elevation view, partly in section, of a photometer construction for use in the instrument of FIG. 8.

FIG. 9 illustrates one construction for a photometer 210 for use in the assembly 208 of FIG. 8. The construction employs a photometer body 212 channeled at its upper surface to seat below the upper flight of conveyer 172 and receive the succession of cuvette vessels 174. An optical source 214 provided by a lamp and reflector directs light through a collimating lens 216, through a heat absorbing filter 218, and directs it to the input facet of a beam splitting bifurcated quartz light pipe 220. One of the two resultant light beams travels through the light pipe leg 220A which directs it to the cuvette chamber, along the longitudinal axis thereof. This beam passes through the liquids in the chamber, through a filter 222 mounted with other filters in a revolving disc 224 driven by a motor 226. A further light pipe 228 directs the resultant light to a measuring detector 230. The other path through the beamsplitting light pipe 220 is directed thereby through filter 232, also on the revolving disc 224, and by a light pipe 234 to a reference detector 236. This dual beam system thus provides measurement of light within the reacting liquids with reference to the light emitted by the source, as sensed with the reference detector 236.

The filter wheel 224 interrupts the two light beams with multiple filter pairs 222, 232. Hence, multiple light absorption measurements can be made for the liquids within a cuvette vessel 174, as various filter pairs interrupt the light beams. The identity of the filter pair(s) 222, 232 appropriate for the chemical test being performed in a given cuvette vessel 174 is stored in the control and processing computer 209 for the FIG. 8 instrument. According to one manner of operation, as the filter wheel revolves, each filter pair interrupting the dual light beam is identified, and as each appropriate or selected filter pair moves into operative position, the computer causes the acceptance and processing of the electrical signals which the detectors 230 and 236 produce. Detector signals produced with inappropriate filters are ignored. Another operational mode is to drive the filter wheel with a motor 226 which can step the wheel from one predetermined shaft position to another, and thereby position a specific filter pair in the light beams for each observational period.

With further reference to FIG. 9, the elements of the photometer 210 are enclosed with a light-tight enclosure 238 to minimize stray light leakage to the detectors. The conveyer-carried cuvette vessel 174 is also covered by a light shield 240 to minimize the entry of stray light into the photometric system.

With reference again to FIG. 8, the photometer assembly 208 employs a single photometer 210 constructed as shown in FIG. 9 and slidably positioned with respect to the conveyer 172, for example mounted on rails or a like mounting carriage. A motor drive moves the single photometer 210 back and forth along the conveyer 172. As the photometer passes each cuvette vessel, the computer operates it to secure another measurement on that cuvette vessel.

In another embodiment, also with reference to FIG. 8, a number of photometers, each typically constructed as shown in FIG. 9, can be positioned at various points along the conveyer 172. As the cuvette vessels advance along the conveyer passed the several photometers, multiple photometric observations are made of the reaction progress in each cuvette vessel.

While many combinations of conveyer and photometer speeds exist for the instrument of FIG. 8, the principles can be illustrated as follows with further reference to FIGS. 8 and 9. The cuvette vessels are advanced in step-like fashion along the conveyer, and each advance cycle consists of two phases. During the first, the cuvette is moved rapidly to the next incremental position along the conveyer. In the other phase, typically somewhat longer, the cuvette is physically static and measurements are made. The photometer assembly begins a scanning motion coincidentally with completion of the first advancement phase, and passes all cuvette vessels in the time interval while the vessels are at rest. This provides an observation of the reaction in each cuvette vessel once in each operating cycle. The photometer is then returned to its original position during the first portion of the next instrument cycle, when the cuvette vessels are advancing. This operating manner secures many data points for monitoring closely the progressive reaction development in each cuvette vessel in the photometer zone of the analysis instrument.

Further, the photometer systems described herein make it practical for an instrument according to the invention to commence the photometric measurement early in the processing of each sample. In addition to providing a substantially complete record of each reaction, the instrument can apply this measuring practice to note an out-of-range test point immediately. In response, the instrument can automatically interrupt its normal routine to draw another liquid sample portion from the sample tray, and process it with selected different dilution. The instrument can monitor measurements made on both of the sample portions it is processing, to provide a correct measure or to initiate other programmed sub-routines for correcting the abnormal measurement.

It will thus be seen that the objects set forth above, among those made apparent from the preceding description, are efficiently attained. Since certain changes may be made in the above constructions without departing from the scope of the invention, it is intended that all matter contained in the above description or shown in the accompanying drawings be interpreted as illustrative and not in a limiting sense.

It is also to be understood that the following claims to cover all of the generic and specific features of the invention described herein, and all statements of the scope of the invention which, as a matter of language, might be said to fall therebetween.

Having described the invention, what is claimed as new and secured by Letters Patent is:

1. In automated sample analysis apparatus for analyzing each of a plurality of samples successively and in liquid state for at least one constituent, said apparatus having (i) sample containers on a first transport,
(ii) reaction vessels and optical cuvette elements on a second transport,
(iii) reagent containers on a third transport,
(iv) liquid transfer means, and
(v) measuring means,
the improvement wherein
said second transport conveys said reaction vessels and said cuvette elements in separate respective single ordered successions successively along a first path,
said third transport conveys said reagent containers along a second path coextensive at least in part with said first path,
said liquid transfer means are arranged for transferring liquid from sample containers on said first transport to reaction vessels being conveyed along said first path, and are arranged for transferring liquid between containers on said third transport and reaction vessels conveyed along said first path at any of plural locations where said second path is coextensive with said first path, and
said measuring means includes photometer source means arranged for illuminating said cuvette elements with optical measuring energy at different locations along at least a selected part of said first path, and further includes photometric detector means and detector carriage means, said carriage means being arranged for carrying said detector means, relative to said second transport, about a path extending along at least a part of said first path receiving radiant energy responsive to illumination of said cuvette elements by said optical source means.

2. In apparatus according to claim 1
the further improvement
wherein said second transport conveys reaction vessels along said first path between at least a sample-receiving location, a reagent-receiving location, and at least one measuring location, and
wherein said second path of said third transport is coextensive with said first path along at least said sample-receiving, reagent-receiving and one measuring locations.

3. In apparatus according to claim 1
the further improvement wherein
said second transport is rotatable and said first path if circular, and
said third transport is rotatable circumferentially around said second transport and said second path is circular.

4. In automated sample analysis apparatus for analyzing each of a plurality of samples successively and in liquid state for at least one constituent, said apparatus having
(i) sample containers on a first transport,
(ii) reaction vessels conveyed along a first path on a second transport,
(iii) reagent containers on a third transport, and
(iv) liquid transfer means arranged for transferring liquid from sample containers on said first transport to reaction vessels on said second transport, and for transferring liquid between containers on said third transport and reaction vessels on said second transport,
the improvement comprising
means forming plural optical cuvette elements on said second transport, each cuvette element being associated with a reaction vessel,
first liquid conduit means connected between each reaction vessel and the associated cuvette element for the passage therethrough of liquid reactants,
second liquid conduit means connected with each cuvette element for communicating a pressure condition applied thereto for selectively passing fluid between that cuvette element and the associated reaction vessel, and
measuring means including photometer source means arranged for illuminating said cuvette elements with optical measuring energy at different locations along at least a selected part of said first path, and further including photometric detector means and detector carriage means, said carriage means being arranged for carrying said detector means about a path extending along at least a part of said first path for receiving radiant energy responsive to illumination of said cuvette elements by said optical source means.

5. In automated sample analysis apparatus for analyzing each of a plurality of samples successively and in liquid state for at least one constituent, said apparatus having
(i) sample containers on a first transport,
(ii) reaction vessels conveyed along a first path on a second transport,
(iii) reagent containers on a third transport, and
(iv) liquid transfer means arranged for transferring liquid from sample containers on said first transport to reaction vessels on said second transport, and for transferring liquid between containers on said third transport and reaction vessels on said second transport,
the improvement comprising
means forming plural optical cuvette elements on said second transport, each cuvette element being associated with a reaction vessel and being arranged for receiving liquid reactants from the associated reaction vessel, and
measuring means including a single photometer source means arranged for illuminating all said cuvette elements with optical measuring energy at different locations along at least a selected part of said first path, and further including photometric detector means and detector carriage means, said carriage means being arranged for carrying a single detector means about a path extending along at least a part of said first path for receiving radiant energy responsive to illumination of all said cuvette elements by said optical source means.

6. In apparatus according to claim 5 the further improvement comprising means for directing optical energy from said source means through each cuvette element selectively along any of two transverse optical paths, and for directing optical energy from any of said optical paths to said single detector means.

7. Photometer apparatus for the repeated measurement of plural samples in succession, said apparatus having a single optical source and plural circularly-arrayed cuvette elements each of which is arranged for receiving optical energy from said source, said apparatus further having the improvement comprising
a single optical detector, and
carriage means for carrying said detector along a circular path for receiving optical energy from each of different sets of one or more of said cuvette elements one at a time and in succession, said received energy being responsive to illumination from said optical source, said carriage means maintaining a selected face of said detector at a selected radial orientation relative to said circular path throughout the movement of said detector along said circular path.

8. Photometer apparatus for the repeated measurement of plural samples in succession, said apparatus having a single optical source, and an ordered and circularly-arrayed set of plural cuvette elements each of which is arranged for receiving optical energy from said source, said apparatus further having the improvement comprising
A. a single optical detector located outside the circular array of said cuvette elements and arranged for receiving optical energy from each of different sets of one or more cuvette elements one at a time and in succession and repeatedly at multiple spaced times throughout an operating time, said received energy being responsive to illumination from said optical source, and
B. means for selecting at least the wavelength of the path through each cuvette element of optical source energy being detected.

9. Automatic photometer apparatus having an optical source and a cuvette with an optical axis between opposed optical windows and an optical detector and means for supplying sample liquid to the cuvette and for discharging sample liquid from it, and having means for directing optical energy from the source to the cuvette along a first direction to illuminate sample therein and to direct resultant optical energy exiting from the cuvette along the first direction to the optical detector, and further comprising
A. first optical means for directing optical energy from the source to the cuvette to illuminate sample therein along a second direction transverse to said first direction, B. second optical means for directing to the detector optical energy exiting from the cuvette along the second direction, and C. selecting means for directing to the cuvette optical energy from the source along only one of said first and second directions, and for directing to the optical detector optical energy exiting from the cuvette along only one of said first and second directions.

10. Photometer apparatus according to claim 9 further comprising first and second further optical windows in said cuvette aligned opposite one another along said second direction and each being in optical alignment with said same-numbered optical directing means.

11. Photometer apparatus according to claim 9 further comprising

A. first housing means mounting said cuvette and said first optical directing means, B. second housing means mounting said detector and said second optical directing means, and C. means mounting said first housing means and said second housing means for rotation relative to one another.

12. Photometer apparatus according to claim 9 further comprising

A. a plurality of said cuvettes,

B. a plurality of said first optical directing means, each of which is associated with one said cuvette, said first directing means being arranged for operative optical alignment with said optical source and with the associated cuvette.

* * * * *

UNITED STATES PATENT AND TRADEMARK OFFICE
CERTIFICATE OF CORRECTION

PATENT NO. : 4,325,910
DATED : April 20, 1982
INVENTOR(S) : Michael Jordan

It is certified that error appears in the above-identified patent and that said Letters Patent are hereby corrected as shown below:

Column 3, line 16, change "fuid" to --fluid--.

Column 4, line 19, change "o" to --of--.

Column 5, line 10, change "conditiong" to --conditioning--.

Column 5, line 68, before "measured" insert --is--.

Column 13, line 50, change "cnjunction" to --conjunction--.

Column 15, line 62, change "tthe" to --the--.

Column 16, line 45, change "devices" to --device--.

Signed and Sealed this

Third Day of May 1983

[SEAL]

*Attest:*

GERALD J. MOSSINGHOFF

*Attesting Officer*     *Commissioner of Patents and Trademarks*